United States Patent [19]

Ekins

[11] Patent Number: 5,599,720
[45] Date of Patent: Feb. 4, 1997

[54] MEASUREMENT OF ANALYTE CONCENTRATION

[75] Inventor: Roger P. Ekins, London, England

[73] Assignee: Multilyte Limited, London, United Kingdom

[21] Appl. No.: 261,757

[22] Filed: Jun. 17, 1994

Related U.S. Application Data

[63] Continuation of Ser. No. 20,872, Feb. 19, 1993, which is a continuation of Ser. No. 533,689, Jun. 5, 1990, abandoned, which is a continuation of Ser. No. 804,305, Dec. 3, 1985, abandoned, which is a continuation-in-part of Ser. No. 606,822, Apr. 24, 1984, abandoned.

[30] Foreign Application Priority Data

Aug. 27, 1982 [GB] United Kingdom ............... 8224600

[51] Int. Cl.$^6$ .................. G01N 33/566; G01N 21/76; G01N 33/543; G01N 33/53
[52] U.S. Cl. ................... 436/501; 436/172; 436/518; 436/528; 436/532; 436/546; 436/810; 435/7.1; 435/7.8; 435/309.1; 435/805
[58] Field of Search ...................... 435/7.1, 7.8, 295, 435/805; 436/501, 518, 528, 532, 546, 172, 810

[56] References Cited

U.S. PATENT DOCUMENTS

| | | | |
|---|---|---|---|
| 4,108,974 | 8/1978 | Wegfahrt et al. | 436/527 |
| 4,256,724 | 3/1981 | Rutner et al. | 422/57 |
| 4,299,916 | 11/1981 | Litman et al. | 435/805 |
| 4,315,907 | 2/1982 | Fridlender et al. | 422/61 |
| 4,381,291 | 4/1983 | Ekins | 436/518 |
| 4,438,067 | 3/1984 | Siddigi | 422/57 |
| 4,444,880 | 4/1984 | Tom | 436/810 |
| 4,698,298 | 10/1987 | Dedieu et al. | 436/531 |
| 4,842,995 | 6/1989 | Iaccheri et al. | 436/808 |
| 4,853,325 | 8/1989 | Vodian | 436/810 |
| 5,171,695 | 12/1992 | Ekins | 436/501 |

FOREIGN PATENT DOCUMENTS

| | | | |
|---|---|---|---|
| 0015687 | 2/1979 | European Pat. Off. | G01N 33/56 |
| 0113075 | 7/1984 | European Pat. Off. | |
| 2029011 | 3/1980 | United Kingdom | G01N 33/50 |
| 8401031 | 3/1984 | WIPO | G01N 33/54 |

OTHER PUBLICATIONS

Ekins, R. P. et al, J. Endocrinol., 85(2)(1980), pp. 29P–30P.
Han, R et al, Radiol. Iugosl., 15(3) (1981), pp. 379–382.
Nisonoff et al, 1958. Heterogeneity and average combining constants of antibodies from individual rabbits. J Immunol. 80:417–28.
Pinckard, 1978. "Equilibruim dialysis and preparation of hapten conjugates" in *Handbook of Experimental Immunology. vol. 1. Immunochemistry*, (D. M. Weir, ed). Blackwell Scientific Publications, Oxford pp. 17.1–17.23.

*Primary Examiner*—Michael P. Woodward
*Attorney, Agent, or Firm*—Dann, Dorfman, Herrell and Skillman

[57] ABSTRACT

A method of measuring the ambient concentration in a fluid, especially a body fluid, of an analyte, such as a hormone or other biologically active material, whose concentration in the fluid is dependent on thedilution of the fluid is disclosed. The fluid is contacted with a trace amount of a binding agent, such as an antibody, specific for the analyte, the proportional occupancy of binding sites on the binding agent is determined and from that figure the analyte concentration is estimated without the need to measure accurately beforehand the volume of the fluid or fluid sample being tested. It is therefore possible to design a concentration-measuring device for insertion into a body fluid of a living creature for in situ measurement of concentration.

19 Claims, 1 Drawing Sheet

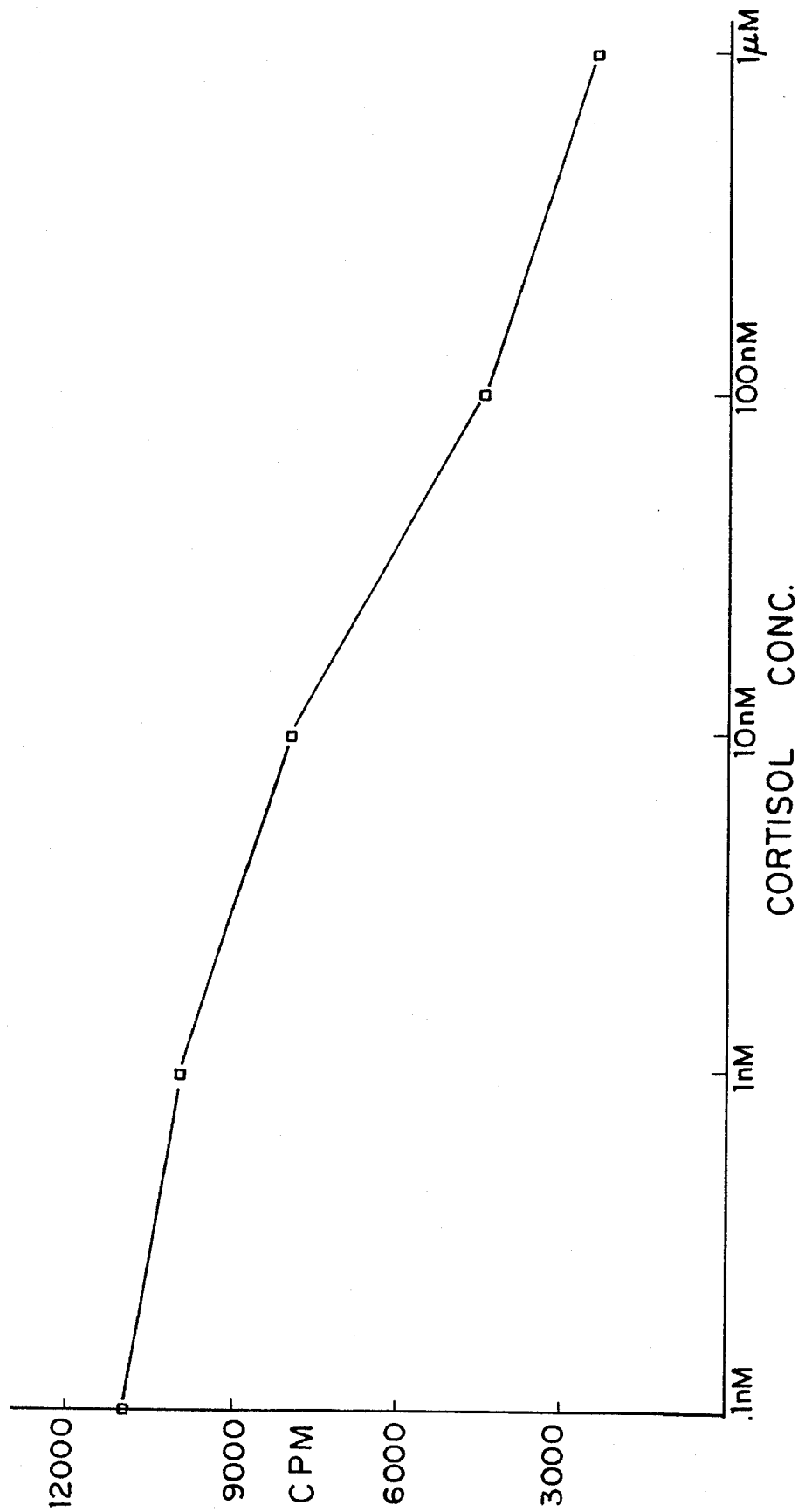

MEASUREMENT OF ANALYTE CONCENTRATION

This is a continuation of co-pending application Ser. No. 08/020,872, filed Feb. 19, 1993; which is a continuation of U.S. Ser. No. 07/533,689, filed Jun. 5, 1990, now abandoned; which is a continuation of U.S. Ser. No. 06/804,305, filed Dec. 3, 1985, now abandoned, which is a continuation-in-part of U.S. Ser. No. 06/606,822, filed Apr. 24, 1984, now abandoned.

TECHNICAL FIELD

The present invention relates to the measurement of ambient analyte concentrations in fluids, primarily the concentrations of hormones and other biologically active substances in body fluids, namely fluids present naturally in living patients, especially human beings, such as saliva, serum, blood and urine.

BACKGROUND ART

The general techniques of the use of radioimmuno-assay are well known, for example from "Radioimmunoassay methods" ed. K. E. Kirkham and W. M. Hunter, Churchill Living stone, Edinburgh (1971) and "Protein and Polypeptide Hormones" ed. M. Margoulis, Excerpta Medica Foundation, Amsterdam (1969), the contents whereof are incorporated herein by reference. It is known from those works and other later publications to measure the concentration of hormones in body fluids in vitro (i.e. external to the body) by contacting a known volume of a sample of the body fluid withdrawn from the body with a binding agent having bindingsites specific for the hormone, usually an antibody, and radioactively labelled hormone. The binding agent binds a proportion of the unlabelled hormone and a proportion of the labelled hormone, the relative amount of labelled hormone bound being a function of the amount of unlabelled hormone present in the sample. The results obtained are calibrated by comparison with the results obtained with standard solutions containing known concentrations of unlabelled hormone, and thus the actual amount of unlabelled hormone in the unknown sample is determined.

Hormones occurring in body fluids can be present in such fluids in free, unbound state alone or both unbound and reversibly bound to proteins or other naturally present binding substances. When a body fluid contains a mixture of free, unbound hormone and reversibly bound hormone, as is the case for example with thyroxine (T4) and triiodothyronine (T3), dilution of a sample of the body fluid does not in general significantly alter the concentration of free hormone because a proportion of the reversibly bound hormone dissociates to liberate free hormone in order to maintain the free hormone concentration. Thus the relative amounts of free and bound hormone are altered rather than the free hormone concentration.

When measuring free hormone in body fluids also containing reversibly bound hormone by a known method, for example by the method described in my U.S. Pat. No. 4,381,291 assigned to A. B. Fortia or in associated publications such as the article by me and my co-workers, S. Filetti, A. B. Kurtz and K. Dwyer in J. Endocrinol., 85(2), pages 29–30 (1980), the relative constancy of the free hormone concentration with dilution makes it relatively unimportant to know the exact volume of the sample of body fluid being assayed and hence the degree to which it will be diluted during the assay.

However, when the hormone or other substance to be assayed in the body fluid is not present in such a reversibly bound form in addition to a free form it has hitherto been believed that it is essential to measure the volume of the fluid sample accurately because any dilution will clearly affect the concentration of the substance being assayed. This belief has meant that assays have always bad to be performed in vitro on an accurately determined volume of a sample of the body fluid in question withdrawn from the body and placed in a test tube or the like.

I have now found that the ambient concentration of an analyte, such as a hormone, in a fluid can be measured without the need to know the volume of the fluid being measured and hence, in the case of body fluids, without the need to remove the body fluid from the body, even when the analyte in question is not present in the fluid as part of an equilibrium system between free and reversibly bound analyte.

This invention is based on the fact, not hitherto appreciated, that when a fluid containing an analyte such as a hormone whose concentration is dependent on the dilution of the fluid is contacted with an antibody or other binding agent having binding sites specific for the analyte, the occupancy of the binding sites by the analyte (i.e. the proportion of binding sites occupied by the analyte on the binding agent) is independent of the absolute volume of the fluid and the absolute number of binding sites, and hence independent of the absolute amount of binding agent, provided only that the relative amounts of analyte and binding agent and the affinity between them are such that the introduction of the binding agent into the fluid has no significant effect on the amount of the analyte remaining unbound. Thus, if only a trace amount of binding agent is used, such that only an insignificant fraction of the analyte becomes bound to the binding agent, then the overall analyte concentration in the fluid will not change noticeably.

Provided that the above condition holds, the concentration [H] of analyte in the fluid is related to the fraction of binding sites occupied ($Ab/Ab_o$) by the equation $$\frac{Ab}{Ab_o} = \frac{K_{ab}[H]}{1 + K_{ab}[H]}$$

where $K_{ab}$ is the equilibrium constant for the binding of the analyte to the binding sites and is a constant for the given analyte and binding agent at a given temperature.

A close analogy to this basic idea is provided by the use of a simple thermometer for the measurement of ambient temperature. The introduction of a thermometer into—for example—a room generally implies uptake of heat by the thermometer and hence a (usually insignificant) disturbance to the pre-existing temperature of the room. Provided that the thermal capacity of the room and its contents are large as compared with that of the thermometer, the temperature ultimately recorded by the thermometer essentially reflects the original room temperature. Likewise the binding-site occupancy of an antibody or other binding agent probe introduced into a biological or other fluid will, assuming the conditions mentioned above are adhered to, reflect the analyte concentration originally present in the fluid.

Accordingly it is possible to design a probe which contains immobilised binding agent in low concentrations, to insert this into the fluid whose ambient analyte concentration is to be measured and, once equilibrium has been reached, to determine the proportion of antibody sites occupied by the analyte. Such a determination will frequently be performed on the probe after withdrawal from the fluid, although this is not an essential feature of the invention, and it would be advantageous in some cases to make the determination in situ and perhaps to couple it with feed-back measures to correct any imbalance of analyte concentration detected, for example to maintain a particular hormone level in a body fluid.

Therefore, the present invention provides in broad terms in one aspect a method of measuring the ambient concentration in a fluid of an analyte whose concentration in that fluid is dependent on the dilution of the fluid, the method comprising contacting a volume of the fluid which has not been accurately measured with a trace amount of binding agent having binding sites specific for the analyte as compared with the other components of the fluid, determining the proportional occupancy of the binding sites on the binding agent by the analyte and estimating from it the concentration of analyte in the fluid. In this context the term "trace" denotes an amount which has only an insignificant effect on the total ambient concentration of analyte in the fluid.

The method may be used for the estimation of analytes of all types provided that a specific binding agent is available and that the analyte concentration in the fluid in question is dependent on the dilution of the fluid. However, it is likely to be of greatest value in the estimation of biologically active materials such as drugs, viruses and particularly hormones, where other estimation methods are more complex. The analytes may be present in any fluid from simple aqueous solutions up to biological fluids of all types but estimation of concentrations in body fluids provides a particularly important area. The presence or absence of other ingredients is immaterial provided that they do not interfere with the binding of the analyte and that they do not provide a sequestered reservoir of the analyte being estimated that is capable of releasing additional analyte as the fluid is diluted. Thus, the method is not intended for use in the estimation of free hormones in fluids which also contain reversibly, endogenously bound hormones. An example of a hormone which has been successfully estimated using the invention is cortisol in saliva. In general, steroid hormones can be similarly estimated in saliva and urine as can drugs such as anabolic steroids (e.g. in the "dope" testing of athletes). In serum, however, these materials tend to be present equilibrium with materials reversibly bound to binding protein. Analytes which can be measured in serum include the protein hormones such as insulin and gonadotrophin, which do not normally occur in saliva.

The analytes may in theory be present in the fluids at any concentration level. The invention is however particularly important in the measurement of very low concentrations such as are typically found for many hormones in body fluids, for example in amounts of 100 picamoles per litre ($10^{-9}$ molar) up to 100 micromoles per litre ($10^{-4}$ molar), especially $10^{-8}$ to $10^{-5}$ molar.

A wide variety of binding agents may also be used provided that they have binding sites which are specific for the analyte in question, as compared with any other ingredient in the fluid in question. When estimating concentrations of hormones or other naturally occurring body chemicals it may be advantageous to use antibodies for the chemical in question where as is often the case these are readily obtainable, e.g. commercially. However, other binding agents such as binding proteins or receptor preparations (preparations containing receptor sites and derived from areas of the body where the chemical in question normally becomes bound) may also be used.

As stated, only a trace amount of binding agent should be used, so that it has only an insignificant effect on the total concentration of analyte in the fluid. Addition of any amount of the binding agent will cause some of the analyte to become bound to the binding sites of the binding agent and this will reduce the amount that is not so bound and hence the concentration. The extent of reduction in concentration that can be tolerated is dependent on the accuracy to which concentration levels can be measured and the accuracy to, which it is desired to measure them. These will vary depending on the analyte, the binding agent and the purpose for which the measurement is to be used. It is believed to be within the competence of a worker in the field to determine the level of accuracy and hence the maximum amount of binding agent permitted in any particular instance, but in general the use of binding agent in an amount sufficient to bind more than 5% of the analyte in the fluid is to be avoided and figures up to 1 or 2% may be preferred.

Conveniently, the binding agent used will be immobilised on a solid support (although soluble binding agents could be used and later precipitated or otherwise separated to enable the binding site occupancy to be estimated). The binding agent may be immobilised by non-specific adsorption onto the support or by covalent bonding to the support. Techniques for immobilising binding agents on supports are known in the art and are described for example in U.S. Pat. Nos. 4,399,217, 4,381,291, 4,357,311, 4,343,312 and 4,260,678, which are incorporated herein by reference. Such known techniques can be used in this invention. When the solid support is polytetrafluoroethylene it has been found possible to couple hormone anti-bodies onto the support by activating the support using sodium and ammonia to aminate it and covalently bonding the antibody to the activated support by means of a carbodiimide reaction (see article by yon Klitzing, Schultek, Strasburger, Fricke and Wood in "Radioimmunoassay and Related Procedures in Medicine 1982", International Atomic Energy Agency, Vienna (1982), pages 57–62.).

The solid supports used may be those which are conventional for this purpose, including cellulose, polysaccharide such as Sephadex (Registered Trade Mark), the supports mentioned in the above-mentioned documents and the like. When, according to a preferred embodiment of the invention, the concentration of an analyte in a body fluid is to be estimated without removing the body fluid from the body, the support should be one which is known to be harmless to the patient and may be in any form convenient for insertion into an appropriate part of the body. For example it may be a probe made of polytetrafluoroethylene, polystyrene or other rigid non-harmful plastics material and having a size and shape to enable it to be introduced into a patient's mouth for estimation of steroid or other hormone concentration in saliva. The selection of an appropriate inert support is within the competance of those skilled in the art, as are its dimensions for the intended purpose.

The amount of binding agent deposited on the solid support will be selected so as to meet the requirement for use of a trace amount relative to the fluid, as explained above. When the binding agent is to be introduced on the solid support into a patient's body the binding agent will naturally be one which is not harmful to the patient in the amounts used and under the conditions to which it is subjected in use (pH etc.) and care will be taken to avoid the presence or retention of harmful substances in the body. The binding agent must as stated above be one which is specific to the analyte as compared to all other materials it is likely to encounter in use so that no interfering reaction or inactivation occurs but this problem is no different in principle from those faced in in vitro assays of body fluids and successfully solved. The choice of a binding agent satisfying these criteria is thus within the general competence of those skilled in the art. When the binding agent is deposited in an amount which is much less than the capacity of the support to adsorb or bond such agents it may be desirable to satisfy the remainder of the adsorption capacity of the support with a harmless protein or immunoglobulin or other inert material not reacting with the analyte nor harmful to the patient (if the solid support is to be inserted in the patient's body). Such materials and the means of applying them to the support are well known and standard methods can be used in this invention. The resulting support containing immobilised binding agent can be stored in dry conditions under temperatures such as are known to be satisfactory for the storage of the known binding agents and will remain stable for extended periods of time, in the same way as commercially available hormone-measuring kits many of which already include hormone antibodies immobilised on a support.

Preferably the binding agent chosen will be one whose equilibrium constant $K_{ab}$ (otherwise known as its affinity constant) in the above equation is such that the proportion of binding sites occupied by the analyte at its expected concentration in the fluid will be considerably less than 100%, more preferably less than 90%, for example less than 75%. This gives greater sensitivity to variations in concentration. When the occupancy of binding sites is measured after equilibrium has been reached or approached, proportional occupancies of 90% and 75% are equivalent to values of Ab/Abo in the above formula of 0.9 and 0.75, respectively. It follows that the equilibrium constant $K_{ab}$ of the binding agent is more preferably less than 9 times the reciprocal of the expected concentration of analyte in the fluid, for example less than 3 times that reciprocal. When the occupancy is measured considerably before the attainment of equilibrium the measured occupancy will be less than the equilibrium figure so that it is then possible to use a binding agent of higher equilibrium constant. Nevertheless, whether the occupancy is measured at equilibrium or beforehand, the binding agent chosen will normally be different in its thermodynamic characteristics from the antibody chosen for use in known radioimmunoassay determinations of hormone concentration, where it is desirable to have as high an occupancy of binding sites on the antibody, and hence as high an equilibrium constant, as possible. In known radioimmunoassays of total hormone the antibody affinity constant is maximized and the amount optimized, whereas according to preferred embodiments of the present invention the affinity constant is optimized and the amount is minimized.

When the occupancy of binding sites on the binding agent is to be determined by methods involving binding the unoccupied sites with a reagent whose presence is discernible, for example a radioactively labelled form of the analyte, the equilibrium constant $K_{ab}$ is preferably such that a substantial proportion of the binding sites are occupied, advantageously at least 25%, i.e. for measurements under equilibrium or approximately equilibrium conditions Ab/Abo in the above formula is at least 0.25—equivalent to at least one third of the reciprocal of the expected concentration of analyte—, because this gives greater sensitivity in the final measurement. For measurements under equilibrium or approximately equilibrium conditions the equilibrium constant $K_{ab}$ of the binding agent is preferably close to the reciprocal of the expected analyte concentration because this will lead to a binding site occupancy close to 50% (i.e. Ab/Abo is close to 0.5).

Affinity constants for many commercially available binding agents are already a matter of record. If the constant is not already known for a particular antibody it may be determined by a standard Scatchard analysis, described originally in Ann. N.Y. Acad. Sci., 51, (1949), 660. Frequently, especially when estimating analytes naturally present in biological fluids, a concentration range within which the analyte concentration is expected to fall will be known before the assay is begun (because normal, healthy patients have a particular concentration level and the assay is intended primarily to discover anomalously high or low concentrations). If so, the choice of a binding agent for the method is a straightforward matter. If the concentration is completely unknown before the initial measurement it may be necessary to select an initial binding agent of arbitrary equilibrium constant, to measure the concentration of analyte approximately using it and then either to select another binding agent of affinity constant closer to the optimum or (if the affinity constant is high) to make measurements at an earlier stage before equilibrium is reached, in order to obtain a more accurate value for the analyte concentration in a repeat procedure.

The nature of the method of estimating the occupancy of binding sites on the binding protein is not an essential part of the present invention in its broadest form and a variety of known methods can be used. The simplest of these is a back-titration of unoccupied sites by the use of a labelled reagent which binds with unoccupied sites but it is also possible to use a sandwich-type or two-site approach. Such methods are disclosed in profusion in the literature, including the books mentioned above and my U.S. Pat. No. 4,381,291 also mentioned above. Alternatively, the extent of occupancy can be measured by biochemical or other means in situ.

Where back-titration assay methods are being used, it is preferred to use a binding agent whose dissociation rate constant for the uncoupling of analyte is low in order to avoid measurement errors as a result of premature dissociation of the analyte from the binding agent. If the rate at which equilibrium is reached is inconveniently slow, it is also possible to make measurements before equilibrium is reached and to deduce from them in known manner the concentrations involved. However in that event it is necessary to measure the period of exposure of the binding agent to theanalyte and any errors in measurement of that period will be transformed into errors in the estimate of analyte concentration, so that this adds to the complexity of the operation and can reduce the accuracy.

With the use of small amounts of binding agent for the test methods it becomes of greater importance to have a labelled reagent of high specific activity for the back-titration to determine the proportion of unoccupied binding sites because, in general, only small absolute numbers of occupied and unoccupied binding sites will be present. Accordingly, instead of conventional radioisotopic labels it may be desirable to employ labels of other types such as fluorescent labels. The use of fluorescent labels is also known in the art and is described for example in published European Patent Applications Nos. 2,963 and 64,484 and U.K. Specification 1,560,402, the contents of which are incorporated herein by reference.

An added advantage of the use of fluorescent labels or others of very high specific activity for analyte-labelling is that they make possible the development of very high sensitivity, multiple-analyte, assays relying on the scanning of the distribution of fluorescent labels (comprising labelled antibodies and/or labelled analytes) deposited on the surface of—for examaple—a suitable plastics material. Such a surface—"printed" with a mixture of different antibodies and subsequently exposed to the biological fluid under test—can potentially be used to reveal the concentrations of many different analytes in the same sample—a requirement which is likely to become increasingly pressing in the monitoring of blood for the presence of complex mixtures of viral antigens and/or antibodies, tumour antigens, hormones etc.

The concept of the "immunometer"—i.e. the analyte concentration sensing device discussed in the preceding paragraph—is likely to bring about significant changes in research and of routine clinical diagnosis. For example, steroid hormone levels may ultimately be monitored —not by in vitro analysis of saliva or blood samples which have been provided by patient, worked up as by freezing and thawing to separate proteins and improve amenability to handling and then accurately measured out to provide a known volume, as is current normal practice—but by examination of the antibody-binding site occupancy of plastic probes following their insertion, for a few minutes, into the subject's mouth, and their exposure to ambient hormone levels present in the saliva. Such methodology is much less likely to be harmful to laboratory staff as droplet formation and the possibility of infection should be reduced.

A simple immunometer according to the invention for in vivo estimation of steroid hormones in saliva is therefore composed of a physiologically harmless solid plastics support of a size and shape to be accommodated in a human patient's mouth and an antibody specific for the steroid hormone to be estimated as compared to other materials encountered in the environment of the mouth immobilised on the support in a trace amount such that when it is inserted into a patient's mouth it will bind less than 5% of the steroid hormone being estimated that is expected to be present in the saliva contained in the mouth.

Such an immunometer will not be harmful to the patient as the extremely small amount of antibody used will not cause toxic or anaphylactic reaction, being in any event firmly immobilised on the support and the support will be no more harmful than the many plastics materials commonly entering patients' mouths as cutlery or the like. The pH conditions encountered in saliva will not inactivate the antibody nor will proteases present in saliva inactivate it within the time span (minutes rather than hours) taken up by the assay.

A device of this construction can also be used in in vitro assays carried out on body fluids or the like, or the size or shape may be modified as appropriate. Such a device can therefore form one part of a kit for the measurement of an appropriate analyte.

The following Examples illustrate the basis for the invention

EXAMPLE 1

Antibody directed against a hormone occurring in a body fluid is diluted in a 0.05M barbital buffer at pH 8.7 and the resulting fluid is exposed to a probe in the form of a plastics support made of polystyrene for 2 to 16 hours at ambient temperature. The plastics support is then removed and thoroughly washed and can then be used as a probe to estimate the concentration of the hormone in appropriate fluids by the method of the invention after its affinity (equilibrium constant) and binding capacity have been assessed by a known method.

EXAMPLE 2

Antibody directed against hydrocortisone (cortisol), obtained from the Tenovus Institute for Cancer Research, Welsh National School of Medicine, Cardiff, Wales, was coupled to a solid support and the equilibrium constant ($K_{ab}$) and binding capacity of the resulting material were measured, by Scatchard analysis, and found to be $2\times10^{10}$ litres/mole and 100 pmoles/ml respectively.

Standard cortisol solutions containing cortisol concentrations of 100 pM, 1 nN, 10 nM, 100 nM and 1 µM were prepared by dissolving pure cortisol (H4001, from Sigma Chemical Co., Poole, England) in a buffer solution of 0.05M $KH_2PO_4$ and 0.15M NaCl (pH 7.4) (hereinafter referred to as PBS) containing 0.1% by weight gelatine (No. 44045, from BDH Chemicals Ltd., Poole, England).

Amounts of the antibody preparation having a binding capacity of less than 10 fmoles of cortisol were incubated to equilibrium at 20° C. (16 hours, although equilibrium had for practical purposes been achieved within 20 minutes) with samples of each of the standard cortisol solutions having volumes of 0.2, 0.4 and 0.8 ml. After incubation the samples were cooled, on ice, to 4° C. and the solid material washed thoroughly with PBS.

The extent of occupancy of the antibody binding sites by cortisol was determined in each case by a radioimmunoassay back-titration using as the labelled material a high specific activity iodinated cortisol (~1000 Ci/m mole $^{125}$I), obtained from RIA Ltd., Cardiff, Wales.

Concentrated $^{125}$I-cortisol was added and mixed with the solid material in each sample and incubation was continued for 1 hour at 4° C. The solid material was again thoroughly washed and the bound radioactivity determined. The accompanying drawing is a graph showing the relationship between the observed radioactivity (in counts per minute) and the cortisol concentration (in nM) of the samples of the standard solutions. Within the limits of experimental error, the level of bound radioactivity was the same for all three samples of identical cortisol concentration and was unaffected by their differences in volume.

EXAMPLE 3

This example describes the use of an immunometer probe to measure the concentration of cortisol in a human patient.

The antibody identified in Example 2 was used in this experiment. It was coupled to the bulbous end of a sterilised polytetrafluoroethylene (TEFLON$^R$) probe in the form of a rod having a length of 15 mm and a diameter of 3 mm with a bulbous end of diameter 5 mm. Bearing in mind that the expected cortisol concentration in the human patient's saliva is about 10 nanomolar and that the amount of saliva to which the probe is likely to be exposed in the mouth during the test is about 3–5 ml, the amount of antibody coupled to the probe was sufficient to provide a binding capacity of about 1 picamol, i.e. sufficient to react with less than 4 per cent of the cortisol expected to be present. The antibody was coupled to the probe by covalent bonding using the method of von Klitzing, Schultek, Strasburger, Fricke and Wood referred to above. It was not necessary to deactivate residual activation sites on the probe.

The probe was then inserted into the patient's mouth and held there until equilibrium was reached. The probe was then removed from the mouth, cooled to 4° C. and washed thoroughly with PBS. The extent of occupancy of the antibody binding sites by cortisol was then determined by a radioimmunoassay back-titration as described in Example 2. The patient suffered no ill effects whatsoever. The results obtained were identical (within the conventional limits of error applicable to assays of this type) with those obtained by a more traditional assay in which the patient spat into a container, the saliva was frozen and thawed to separate out proteins and make it less viscous, the resulting material was contacted with an equivalent amount of the same antibody coupled onto a sol id probe of the same material until equilibrium was reached, the probe was then removed from the sample, cooled, washed with PBS and subjected to radioimmlunoassay back-titration for cortisol estimation as described in Example 2.

These results show that the antibody is not inactivated by proteases in saliva nor by the pH conditions in the mouth, also that there was neither toxic nor anaphylactic shock.

EXAMPLE 4

A fine TEFLON$^R$ plastics probe was coated with hormone antibody and inserted into the vein of a rat and withdrawn after a period of several minutes. No observable physiological and pharmacological changes occured, nor indeed would any have been expected as both TEFLON and hormone antibodies are regularly inserted into animals' bloodstreams separately without harmful effect.

I claim:

1. A method of estimating the concentration in a fluid of an analyte whose concentration in that fluid is dependent on the dilution of the fluid, comprising contacting the fluid with a binding agent having binding sites specific for the analyte, the binding agent being used in a small amount such that the binding agent has at most only an insignificant effect on the ambient concentration of the analyte in the fluid, separating the binding agent and determining a value representative of the proportional occupancy of the binding sites of the binding agent by the analyte, and thereby determining from said value the analyte concentration in the fluid.

2. A method as claimed in claim 1 wherein the analyte is selected from the group consisting of a drug, virus or hormone and the binding agent is an antibody for the analyte.

3. A method as claimed in claim 2, wherein the analyte is a hormone.

4. A method as claimed in claim 3, wherein the hormone is a steroid hormone and the fluid is either saliva or urine.

5. A method as claimed in claim 1 wherein the binding agent is contacted with the fluid whilst immobilised on a solid support, and the binding agent and solid support are separated from the fluid before the value representative of the proportional occupancy of the binding sites is determined.

6. A method as claimed in claim 1, wherein the fluid is a body fluid and binding agent is immobilised on a probe capable of being inserted into and withdrawn from the body fluid.

7. A method as claimed in claim 1, wherein a binding agent is chosen whose equilibrium constant for the binding of the analyte to the binding sites is such that more than about 25% of the binding sites of the binding agent will be occupied by the analyte at its expected concentration in the fluid.

8. A method as claimed in claim 7, wherein a binding agent is chosen whose equilibrium constant for the binding of the analyte to the binding sites is such that less than about 75% of the binding sites of the binding agent will be occupied by the analyte at its expected concentration in the fluid.

9. A method as claimed in claim 1 wherein the value representative of the proportional occupancy of the binding sites on the binding agent is determined by back-titration using a fluorescent labelled reagent.

10. A method as claimed in claim 11 wherein the small amount of said binding agent binds no more than about 2% of the analyte in the fluid.

11. A method of estimating in vivo concentration of an analyte in a body fluid whose concentration is dependent on the dilution of the fluid, without the necessity of measuring the volume of the fluid, comprising contacting the body fluid with a binding agent having binding sites specific for the analyte, the binding agent being used in a small amount such that the binding agent has at most only an insignificant effect on the ambient concentration of the analyte in the body fluid, separating the binding agent and determining a value representative of the proportional occupancy of the binding sites of the binding agent occupied by the analyte, and thereby determining from said value the concentration of analyte in the fluid.

12. A method as claimed in claim 11 wherein the analyte is a steroid hormone.

13. A method as claimed in claim 11 wherein the binding agent has an affinity constant from one third to nine times the reciprocal of the analyte concentration in the saliva of normal, healthy beings.

14. A method as claimed in claim 11 wherein the binding agent is an antibody and is coupled onto a physiologically harmless solid support.

15. A method as claimed in claim 14 wherein the support is polytetrafluoroethylene and the antibody is coupled to it by covalent bonding via a carbodiimide reaction after activation of the support with sodium and ammonia.

16. A method as claimed in claim 11 wherein the valve representative the proportional occupancy of binding sites is determined by back titration using a labelled reagent.

17. A method as claimed in claim 11 wherein the small amount of said binding agent binds no more than about 2% of the analyte in the fluid.

18. A method of estimating the concentration in a fluid of an analyte whose concentration in that fluid is dependent on the dilution of the fluid, comprising contacting the fluid with a binding agent having binding sites specific for the analyte, the binding agent being immobilized on a support and used in a small amount such as to have at most only an insignificant effect on the ambient concentration of the analyte in the fluid, separating the binding agent and determining a value representative of the proportional occupancy of the binding sites of the binding agent occupied by the analyte, and thereby determining from said value the analyte concentration in the fluid.

19. A method of estimating the in vivo concentration of an analyte in a body fluid whose concentration is dependent on the dilution of the fluid, without the necessity of measuring the volume of the fluid, comprising contacting the body fluid with a binding agent having binding sites specific for the analyte, the binding agent being immobilized on a solid support and used in a small amount such as to have at most only an insignificant effect on the ambient concentration of the analyte in the body fluid, separating the binding agent and determining a value representative of the proportional occupancy of the binding sites of the binding agent occupied by the analyte, and thereby determining from said value the concentration of analyte in the fluid.

* * * * *

UNITED STATES PATENT AND TRADEMARK OFFICE
CERTIFICATE OF CORRECTION

PATENT NO. : 5,599,720  
DATED : February 4, 1997  
INVENTOR(S) : Roger P. Ekins Page 1 of 1

It is certified that error appears in the above-identified patent and that said Letters Patent is hereby corrected as shown below:

<u>Column 10,</u>  
Line 5, "11" should read -- 1 --.

Signed and Sealed this

Twenty-fifth Day of May, 2004

JON W. DUDAS  
*Acting Director of the United States Patent and Trademark Office*

(12) EX PARTE REEXAMINATION CERTIFICATE (5659th)
United States Patent
Ekins

(10) Number: US 5,599,720 C1
(45) Certificate Issued: Jan. 23, 2007

(54) MEASUREMENT OF ANALYTE CONCENTRATION

(75) Inventor: Roger P. Ekins, London (GB)

(73) Assignee: Multilyte Limited, London (GB)

Reexamination Request:
No. 90/006,854, Nov. 10, 2003
No. 90/006,961, Mar. 11, 2004
No. 90/007,321, Nov. 23, 2004

Reexamination Certificate for:
Patent No.: 5,599,720
Issued: Feb. 4, 1997
Appl. No.: 08/261,757
Filed: Jun. 17, 1994

Certificate of Correction issued May 25, 2004.

Related U.S. Application Data

(63) Continuation of application No. 08/020,872, filed on Feb. 19, 1993, now abandoned, which is a continuation of application No. 07/533,689, filed on Jun. 5, 1990, now abandoned, which is a continuation of application No. 06/804,305, filed on Dec. 3, 1985, now abandoned, which is a continuation-in-part of application No. 06/606,822, filed on Apr. 24, 1984, now abandoned.

(30) Foreign Application Priority Data

Aug. 27, 1982 (GB) .............................. 8224600

(51) Int. Cl.
*G01N 33/566* (2006.01)

(52) U.S. Cl. ...................... 436/501; 436/172; 436/518; 436/528; 436/532; 436/546; 436/810; 435/7.1; 435/7.8; 435/805

(58) Field of Classification Search ................ 435/7.1, 435/7.8, 7.92; 436/518, 517
See application file for complete search history.

(56) References Cited

U.S. PATENT DOCUMENTS

| | | |
|---|---|---|
| 1,711,742 A | 5/1929 | Nordlander |
| 3,001,915 A | 9/1961 | Fonner |
| 3,802,842 A | 4/1974 | Lange et al. |
| 3,901,067 A | 8/1975 | Boardman |
| 3,907,503 A | 9/1975 | Betts et al. |
| 3,945,798 A | 3/1976 | Young |
| 4,054,646 A | 10/1977 | Giaever |
| 4,108,974 A | 8/1978 | Wegfahrt et al. |
| 4,120,754 A | 10/1978 | Barendsz et al. |
| 4,158,958 A | 6/1979 | Braun |
| 4,160,008 A | 7/1979 | Fenocketti |
| 4,166,767 A | 9/1979 | Kurooka et al. |
| 4,236,893 A | 12/1980 | Rice |
| 4,242,096 A | 12/1980 | Oliveira et al. |
| 4,256,724 A | 3/1981 | Rutner et al. |
| 4,299,916 A | 11/1981 | Litman et al. |
| 4,301,115 A | 11/1981 | Rapkin et al. |
| 4,315,907 A | 2/1982 | Fridlender et al. |
| 4,344,438 A | 8/1982 | Schultz |
| 4,348,358 A | 9/1982 | McKee |
| 4,381,291 A | 4/1983 | Ekins |
| 4,387,165 A | 6/1983 | Youngblood |
| 4,402,819 A | 9/1983 | Rechnitz et al. |
| 4,411,989 A | 10/1983 | Grow |
| 4,436,819 A | 3/1984 | Manning |
| 4,438,067 A | 3/1984 | Siddiqi |
| 4,444,880 A | 4/1984 | Tom |
| 4,487,839 A | 12/1984 | Kamentsky |
| 4,591,570 A | 5/1986 | Chang |
| 4,608,344 A | 8/1986 | Carter |
| 4,647,544 A | 3/1987 | Nicoli et al. |
| 4,673,657 A | 6/1987 | Christian |
| 4,698,298 A | 10/1987 | Dedieu et al. |
| 4,842,995 A | 6/1989 | Iaccheri et al. |
| 4,853,325 A | 8/1989 | Vodian et al. |
| 4,880,750 A | 11/1989 | Francoeur |
| 5,156,953 A | 10/1992 | Litman et al. |
| 5,171,695 A | 12/1992 | Ekins |
| 5,348,855 A | 9/1994 | Dattagupta |
| 5,486,452 A | 1/1996 | Gordon et al. |
| 5,599,720 A | 2/1997 | Ekins |

FOREIGN PATENT DOCUMENTS

| | | |
|---|---|---|
| EP | 0015687 A1 | 9/1980 |
| EP | 015 687 A | 9/1980 |
| EP | A 0026103 | 4/1981 |
| EP | 0063810 | 11/1982 |
| EP | 0015687 | 4/1983 |
| EP | 0 015 687 A | 4/1983 |
| EP | 0134215 B1 | 8/1983 |
| EP | 0113075 | 7/1984 |
| EP | 0235726 | 9/1987 |
| EP | 0 304 202 | 2/1989 |
| GB | 2029011 | 3/1980 |
| GB | 2030290 | 4/1980 |
| GB | A 2085160 | 4/1982 |
| GB | 2 099 578 A | 11/1982 |
| GB | 2099578 A | 12/1982 |
| WO | A 8201773 | 5/1982 |
| WO | 84/01031 | 3/1984 |
| WO | 86/01604 | 3/1986 |
| WO | 84/03151 | 5/1986 |
| WO | 90/15070 | 12/1990 |
| WO | 88/01058 | 2/1998 |

OTHER PUBLICATIONS

Ekins, R P et al., Endocrinology 1980;85(2):29–30.
Han R et al., Radiol. Iugusl., 1981;15(3):379–382 (See English summary at pp. 381–382).

(Continued)

*Primary Examiner*—James Housel

(57) ABSTRACT

A method of measuring the ambient concentration in a fluid, especially a body fluid, of an analyte, such as a hormone or other biologically active material, whose concentration in the fluid is dependent on thedilution of the fluid is disclosed. The fluid is contacted with a trace amount of a binding agent, such as an antibody, specific for the analyte, the proportional occupancy of binding sites on the binding agent is determined and from that figure the analyte concentration is estimated without the need to measure accurately beforehand the volume of the fluid or fluid sample being tested. It is therefore possible to design a concentration-measuring device for insertion into a body fluid of a living creature for in situ measurement of concentration.

OTHER PUBLICATIONS

Nisonoff and Pressman, 1958, "Heterogeneity and average combining constants of antibodies from individual rabbits", J. Immuno. 80:417–428.

Pinckard, 1978, "Equilibrium dialysis and preparation of hapten conjugates" in *Handbook of Experimental Immunology*. vol. 1. *Immunochemistry*, (D.M.Weir, ed), Blackwell Scientific Publications, Oxford pp. 17.1–17.23.

Casall et al., "High–affinity Antibodies to ssDNA are Produced by CD–B Cells in Systemic Lupus Erythematosus Patients," J. Immunol. vol. 143, p. 3476–83 (1989).

Declaration of Edwin F. Ullman from Nullity Action filed Oct. 15, 2003 against the German part of European Patent No. 0134215.

Declaration of Edwin F. Ullman "Ullman II Declaration" filed Feb. 15, 2004 against the German part of European Patent No. 0134215.

D'Auria, et al., "The Fluorescence Emission of the Apo–glucose Oxidase from *Aspergillus niger* as Probe to Estimate Glucose Concentrations", Biomedical and Biophysical Research Communications, vol. 263, p. 550–53 (1999).

Deelder, et al., "Automated Measurement of Immunogalactosidase Reactions with a Fluorogenic Substrate by the Aperture Defined Microvolume Measurement Method and its Potential Application to Schistosoma Mansoni Immunodiagnosis", J. Immunological Meth., vol. 36, p. 269–83 (1980).

Giaever, Ivar, "Visual Detection of Carcinoembryonic Antigen on Surfaces", J. of Immunol., vol. 116 (3), p. 766–771 (1976).

Giaever, Ivar, "The Antibody–Antigen Reaction: A Visual Observation", J. of Immunol., vol. 110 (5), p. 1424–26 (1973).

Harris et al., "Ultrasensitive Enzymatic Radioimmunoassay: Application to Detection of Cholera Toxin and Rotavirus", Proceedings of National Academy of Sciences, vol. 76 (10), p. 5336–39 (1979).

Hawkes et al., "A Dot–Immunobinding Assay of Monoclonal and Other Antibodies", Anal. Biochem., vol. 119, p. 142–47, Fig. 5 (1982).

Litman et al., "An Internally Referenced Test Strip Immunoassay for Morphine", Clin. Chem., vol. 29, p. 1598–1603 (1983).

"Methyl Red", Sigma/Aldridge Catalog.

Modern Urine Chemistry, "A Guide to the Diagnosis of Urinary Tract Diseases & Metabolic Disorders", Ames Division, Miles Labs, p. 28–32 (1976).

Pugia et al., "High–sensitivity Dye Binding Assay for Albumin in Urine", J. Clin. Lab. Anal., vol. 13, p. 180–87 (1999).

Request for Reexamination of U.S. Patent No. 5,599,720 under 35 U.S.C. §302 and 37 CFR §1.501 and §510–Expedited Handling.

Schultz, et al., "Affinity Sensor: A new technique for developing implantable sensors for glucose and other metabolites", Diabetes Care vol. 5 (3), p. 245–53 (1982).

Schultz, et al., "Affinity Sensors for Individual Metabolites", Biotechnology and Bioengineering Symposium, vol. 9, p. 65–71 (1979).

Solsky and Rechnitz, "Antibody–selective Membrane Electrodes", Science, vol. 204, p. 1308–09 (1979).

Suenaga et al., "Lupus–derived Human Monoclonal IgM Anti–DNA Antibody Displays Monospecificity, High–affinity and Private Idiotype Specificity", Lupus vol. 1, p. 363–8 (1992).

Swoboda, et al., "Purification and Properties of the Glucose Oxidase from *Aspergillus niger*", Journal of Biological Chemistry, vol. 240 (5), p. 2209–15 (1965).

The Handbook of Immunoassay, Wild, ed., Nature Publishing Group, p. 55, Fig 3.15 (2001).

"Translation of the Multilyte's response in case 3 filed with the Federal Patent Court on Feb. 9, 2004".

Ullman and Maggio, In: Enzyme Immunoassay, Maggio, ed., CRC Press, p. 110, 189 (1980).

Ullman Graphical Sketch.

Ritzmann, et al, "Serum Protein Abnormalities Diagnostic and Clinical Aspects", by Little Brown and Company, First Edition, p. 314–330 (1975).

Declaration of Edwin F. Ullman from Nullity Action filed Oct. 15, 2003 against the German part of European Patent No. 0134215.

Halfman, Clarke, J. Methods in Enzymology, vol. 74, pp. 481–497 (1981).

Erlanger in Methods in Enzymology, Immunochemical Techniques, vol. 70, Part A, Vienabis et al., 1980, pp. 85, 91–95.

Eisen, Immunology 1980, pp. 298–300, 305.

[Proposed] Fourth Amended Complaint for Declaratory Judgement—Demand for Jury Trial.

Gallo, Dana, et al., J. Clin. Microb., vol. 13, pp. 631–636 (1981).

Scribblers, Calligraphy Catalog, http://www.scribblers.co.uk/acatalog/speedball_C_style_nibs_righthanded.html, May 27, 2004.

Roger Ekins, Assay Design and Quality Control, In: Radioimmunology—1979 (Ch. A. Bizollon, ed.). Elsevier, North Holland Biomedical Press, Amsterdam, Netherlands, pp. 239–255.

Supplementary Declaration of E.F. Ullaman, dated Jun. 1, 2004.

Roger Ekins, Internet Forum on Microarrays and Mass Action Laws, May 14, 2000–May 16, 2000.

Page 11 of Multilyte's submission to the German tribunal presiding over the nullity action.

R. Ekins, et al. Inalytica Chimica Acta, vol. 227, pp. 73–96.

Sokolowski and Wood, Radioimmunoassay in Theory and Practice, In: A handbook for Laboratory Personnel, Schnetztor–Verlag, Konstanz, pp. 138–143 and pp. 172–173.

Declaration of Edwin F. Ullman "Ullman II Declaration", dated Feb. 15, 2004.

Deelder, et al., J. Immunological Meth., vol. 36, p. 269–83 (1980).

Giaver, Ivar, J. of Immunol., vol. 110 (5), p. 1424–26 (1973).

Harris et al., Proceedings of National Academy of Sciences, vol. 76 (10), p. 5336–39 (1979).

Hawkes et al., Anal. Biochem., vol. 119, p. 142–47, Fig. 5 (1982).

"Methyl Red", Sigma/Aldridge Catalog.

Modern Urine Chemistry, Ames Division, Miles Labs, p. 28–32 (1976).

Schultz, et al., Diabetes Care vol. 5 (3), p. 245–53 (1982).

Schultz, et al., Biotechnology and Bioengineering Symposium, vol. 9, p. 65–71 (1979).

Swoboda, et al., Journal of Biological Chemistry, vol. 240 (5), p. 2209–15 (1965).

Ullman Graphical Sketch.

Ritzmann, et al., "Serum Protein Abnormalities Diagnostic and Clinical Aspects", Little Brown and Company, First Edition, p. 314–330 (1975).

Miller et al., Clin, Chem., vol. 30, p. 1467 (1984).

Berson et al., *Methods in Investigative and Diagnostic Endocrinology* p. 111–116 (1973).

Berson et al., *Methods in Investigative and Diagnostic Endocrinology* p. 169–177 (1973).

Dudley et al., *Clin. Chem.,* vol. 31, p. 1264–1271 (1985).

Ekins, *Nature,* vol. 284, p. 14–15 (Mar. 6, 1980).

Ekins et al., *Clin. Chem.,* 39:369–370 (1992).

Ekins, *Nature,* vol. 340, pp. 256–58 (Jul. 27, 1989).

Brown et al., In vitro procedures with radioisotopes in medicine *International Atomic Energy Agency* (1970) [Identified as: "Ekins, In vitro procedures with radioisotopes in medicine *International Atomic Energy Agency* (Jun. 1970) in Appendix A to the Affymetrix Contentions and Prior Art"].

Ekins, The Handbook of Immunoassay. Wild ed. Nature Publishing Group. p. 55, Fig. 3.15 (2001).

Ekins State of the Art, and Perspectives of Immunoassay. *International Symposium on Molecular Proves: Technology and Medical Applications* (Florence, Apr. 11–13, 1988).

Ekins, *Towards Immunoassays of Greater Sensitivity, Spefificity and Speed: An Overview,* Elsevier/North–Holland Biomedical Press, pp. 3–21 (1981).—Including commercially–available free hormone assays cited therein.

Graff, A Handbook of Routine Urinanalysis, Philadelphia: J.B.:o[[omcptt Cp,[amu (1983).

Kabakoff, Enzyme Immunoassay. Maggio ed., CRC Press, p. 80 (1980).

Maggio, Enzyme–Immunoassay, CRC Press, Boca Raton, FL. p. 189, Fig. 5.

Miles et al., *J. Biol. Chem.,* vol. 256, No. 23, pp. 12545–12552 (1981).

Rordorf et al., *J. Immunological Methods,* vol. 59, pp. 105–112 (1983).

Wilkins et al., *Clin. Chem.* vol. 31, No. 10, pp. 1644–1653 (Oct. 1985).

Benton et al., *Science,* vol. 196, pp. 180–182 (1977).

Maniatis et al., Molecular Cloning: A Laboratory Manual (1982).

Southern, *J. Mol. Biol.,* vol. 98, p. 503 (1975).

St. John. T.P. et al., *Cell,* vol. 16, p. 443 (1979).

St. John, T.P., The Organization and Transcription of the Saccharomyces Cerevisiae Galactose Gene Cluster, A Dissertation Submitted to the Department of Biochemistry and the Committee on Graduate Studies of Stanford University in Partial Fulfillment of the Requirements For the Degree of Doctor of Philosophy (May 1980).

"Plaintiff Affymetrix's Preliminary Invalidity Contentions, Identification of Prior Art, and Accompanying Document Production Pursuant to Patent L.R. 3–3 and 3–4".

"Third Amended Complaint for Declaratory Judgement–Demand for July Trial".

Request for Reexamination of U.S. Patent No. 5,599,720 filed by Affymetrix on Mar. 10, 2004.

Sehon, In: Methods in Immunology and Immunochemistry. Ed. Williams and Chase.—NY: Academic Press, (1971). Chapter 15, p. 375–383.

Solsky and Rechnitz, Science, (1979) vol. 204, p. 1308–1309.

Nakamura and Tucker, In: Serum Protein Abnormalities. Ed. Ritzmann and Daniels, Little, Brown, & Co., Boston, (1975). Chapter 17, p. 314–330.

Casali et al., Journal of Immunology, (1989) vol. 143, p. 3476–3483.

Suenaga et al., Lupus, (1992) vol. 1, p. 363–368.

Conway de Macario et al., Journal of Immunol. Methods, (1983), vol. 59, p. 39–47.

Dissanayake et al., Immunology, (1977), vol. 32, p. 309–318.

Vonderviszt et al., Biochem, J., (1987) vol. 243, p. 449–455.

Litman et al., Clin. Chem., (1983) vol. 29, p. 1598–1603.

Ekins et al., In: Alternative Immunoassays, Ed. by. W.P. Collins, NY: Wiley (1985)., Chapter 13, p. 219–237.

Ekins et al., J. Endocrinology, 85(2):29P–30P (1980).

Giaever, Ivar: Journal of Immunology, (1976) vol. 116, No. 3, pp. 766–771.

Fodor et al., Science (1991) vol. 251, p. 767–773.

Pugia et al., J. Clin. Lab. Anal., (1999), vol. 13, p. 180–187.

D'Auria, Biomedical and Biophysical Research Communications (1999), vol. 263, p. 550–553.

Multilyte's opposition to plaintiff/counterdefendant Affymetix Inc.'s motion for summary judgment of noninfringement based on the court's construction of the term "determining the ambient concentrations". Apr. 27, 2005 1:30 PM, Judge Hon. William Alsup.

Multilyte Ltd.'s opposition to Affymetrix, Inc.'s motion for summary judgement of noninfringement based on the construction of the term "binding agent" Apr. 27, 2005, time 1:30PM. Judge Hon. William Alsup.

Multilyte Ltd.'s notice of motion and motion for partial summary judgement for further claim construction of the term "binding agent", Apr. 28, 2005, Judge Hon. William Alsup.

Reporter's Transcript of Proceedings *Affymetrix, Incorporated* vs. *Multilyte, Limited,*. Before the Honorable William Alsup, Judge, Thursday, Feb. 16, 2005. (108 pages).

Multilyte Ltd.s Tutorial—Presentation Slides (95 pgs).

Order construing selected Claims terms (Feb. 22, 2005).

Order granting motion to alter or amend judgment, setting briefing schedule and vacating hearing. (May 17, 2005).

Order granting Summary Judgment of Non–infringement. (Apr. 28, 2005).

Order granting Multilyte's motion for further claim construction and re–construing "binding Agent".

Transcript of Proceedings, Dated Apr. 27, 2005 78 pages.

Albertini et al; "Monoclonal Antibodies and Developments In Immunoassay"; Proceedings of $3^{rd}$ Int. Conference on Radioimmunoassay 1981, Italy, May 6–9; (1981).

Collins et at; "Solid Phase C1q–Binding Fluorescence Immunoassay for Detection of Circular Immune Complexes"; Journal of Clinical Microbiology, Mar. 1982, p. 456–464; (1982).

Uchimura et al; "Measurements of Free Thyroxine: Comparison of Per Cent of Free Thyroxine in Diluted and Undiluted Sera"; JCE & M; vol. 42, No. 3; p. 561–566; (1976).

Wang et al; "A Simplified Solid–Phase Immunofluorescence Assay for Measurement of Serum Immunoglobulins";Clinica Chimica Acta, 102; p. 169–177 (1980).

Response filed Apr. 18, 1985 to Office Action of Oct. 24, 1984 for USSN 606,822.

Deposition of Roger P. Ekins taken Monday, Mar. 8, 2004, in Case No.: C03 3779 WHA.

Translation of Jun. 28, 2004's reply to defendant's rejoinder dated Mar. 12, 2004 for Docket No.: 4b O 268/03.

Translation of Judgment in Patent Nillity Case 3 Ni 40/03 EU concerning EP 0134215, pronounced on Jun. 30, 2004.

EP 0134215 amended claims.

UK Order in Cases HC–03–C0 2951 and HC–03–C0 2952 concerning EP (UK) No. 0 134 215 and EP (UK) No. 0 304 202, pronounced on Sep. 13, 2004.

Edwin F. Ullman Curriculum Vitae.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–19 is confirmed.

* * * * *